United States Patent
Umeda et al.

(10) Patent No.: US 10,319,928 B2
(45) Date of Patent: Jun. 11, 2019

(54) ELECTRODE MATERIAL FOR ORGANIC SEMICONDUCTOR DEVICE

(71) Applicant: FUJIFILM Corporation, Tokyo (JP)

(72) Inventors: Kenichi Umeda, Kanagawa (JP); Keisuke Ushirogata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/673,756

(22) Filed: Aug. 10, 2017

(65) Prior Publication Data

US 2017/0358765 A1 Dec. 14, 2017

Related U.S. Application Data

(63) Continuation of application No. PCT/JP2016/052271, filed on Jan. 27, 2016.

(30) Foreign Application Priority Data

Feb. 27, 2015 (JP) .................................. 2015-038550

(51) Int. Cl.
| | |
|---|---|
| H01L 51/10 | (2006.01) |
| C07D 487/22 | (2006.01) |
| H01L 21/288 | (2006.01) |
| H01L 29/417 | (2006.01) |
| H01L 29/786 | (2006.01) |
| H01L 51/00 | (2006.01) |

(52) U.S. Cl.
CPC .......... *H01L 51/105* (2013.01); *C07D 487/22* (2013.01); *H01L 21/288* (2013.01); *H01L 29/417* (2013.01); *H01L 29/786* (2013.01); *H01L 51/0078* (2013.01); *H01L 51/0091* (2013.01); *H01L 2251/301* (2013.01)

(58) Field of Classification Search
CPC .............................. C07D 487/22; H01L 51/105
See application file for complete search history.

(56) References Cited

U.S. PATENT DOCUMENTS

| 8,309,952 B2 | 11/2012 | Matsubara et al. |
| 2013/0001479 A1 | 1/2013 | Kanehara et al. |
| 2015/0337135 A1 | 11/2015 | Shibata et al. |

FOREIGN PATENT DOCUMENTS

| JP | 2008-85315 A | 4/2008 |
| JP | 2012-069560 A | 4/2012 |
| JP | 2014-236064 A | 12/2014 |
| WO | 2011/114713 A1 | 9/2011 |
| WO | 2014/084331 A1 | 6/2014 |

OTHER PUBLICATIONS

Mugadza, et al. Journal of Colloid and Interface Science 354 (2011) 437-447.*
International Preliminary Report on Patentability dated Aug. 29, 2017 issued by the International Bureau in International Application No. PCT/JP2016/052271.
English Translation of Written Opinion dated Apr. 12, 2016 issued by the International Searchng Authority in International Application No. PCT/JP2016/052271.
International Search Report dated Apr. 12, 2016 issued by the International Searching Authority in International Application No. PCT/JP2016/052271.
Office Action dated Apr. 3, 2018 from the Japanese Patent Office in counterpart Japanese Application No. 2017-501995.
Communication dated Nov. 6, 2018 from the Japanese Patent Office in counterpart Japanese application No. 2017-501995.

* cited by examiner

*Primary Examiner* — Shawquia Jackson
(74) *Attorney, Agent, or Firm* — Sughrue Mion, PLLC

(57) ABSTRACT

An object of the present invention is to provide an electrode material for an organic semiconductor device which maintains excellent conductivity and of which contact properties with an organic semiconductor becomes favorable. The electrode material for an organic semiconductor device of the present invention contains inorganic nanoparticles and an organic π-conjugated ligand, in which the organic π-conjugated ligand is a ligand having at least one electron-withdrawing substituent.

9 Claims, No Drawings

ELECTRODE MATERIAL FOR ORGANIC SEMICONDUCTOR DEVICE

CROSS-REFERENCE TO RELATED APPLICATIONS

This application is a Continuation of PCT International Application No. PCT/JP2016/052271 filed on Jan. 27, 2016, which claims priority under 35 U.S.C. § 119(a) to Japanese Patent Application No. 2015-038550 filed on Feb. 27, 2015. The above application is hereby expressly incorporated by reference, in its entirety, into the present application.

BACKGROUND OF THE INVENTION

1. Field of the Invention

The present invention relates to an electrode material for an organic semiconductor device.

2. Description of the Related Art

A device (hereinafter, also referred to as an "organic semiconductor device") in which an organic semiconductor material is used is attracting great attention since the device is expected to have various advantages compared to a device in the related art in which an inorganic semiconductor material such as silicon is used.

For example, an organic thin film transistor (OTFT) or organic thin film solar cells (organic photovoltaics: OPV) are known as the organic semiconductor device.

It is known that a dispersion (conductive nanoink) containing a dispersion medium and inorganic nanoparticles such as metal nanoparticles is used as a material for forming a conductive circuit and an electrode in such an organic semiconductor device.

For example, WO2011/114713A discloses a "nanoink composition containing inorganic nanoparticles, an organic π-conjugated ligand, and a solvent, wherein the organic π-conjugated ligand is π-bonded to the inorganic nanoparticles and the nanoink composition, has electrical conductivity due to the strong π-bonding and approach between the particles ([claim 1]).

In addition, JP2014-236064A discloses that a rear surface electrode layer is formed in a method for manufacturing an organic thin film solar cell using a dispersion medium containing metal nanoparticles and an organic π-bonded ligand ([claim 1] and [claim 2]).

SUMMARY OF THE INVENTION

The present inventors have conducted studies on the nanoink composition or the dispersion medium disclosed in WO2011/114713A and JP2014-236064A, and as a result, they have found that there is a case where the performance of an electrode deteriorates if the electrode is manufactured using those materials since an energy barrier of charge movement at the interface between the electrode and an organic semiconductor is increased depending on the type of organic π-conjugated ligand, whereas the conductivity is favorable.

In the present specification, an expression that "energy barrier of charge movement becomes low at the interface between an electrode and an organic semiconductor" is also described as "contact properties with an organic semiconductor become favorable".

An object of the present invention is to provide an electrode material for an organic semiconductor device which maintains excellent conductivity and of which contact properties with an organic semiconductor becomes favorable.

The present inventors have conducted extensive studies in order to achieve the above-described object. As a result, they have found that an electrode formed by using inorganic nanoparticles and an organic π-conjugated ligand which has an electron-withdrawing substituent maintains excellent conductivity and contact properties between the electrode and an organic semiconductor become favorable, and have completed the present invention.

That is, the present inventors have found that it is possible to achieve the above-described object using the following configuration.

[1] An electrode material for an organic semiconductor device, comprising: inorganic nanoparticles and an organic π-conjugated ligand, in which the organic π-conjugated ligand is a ligand having at least one electron-withdrawing substituent.

[2] The electrode material for an organic semiconductor device according to [1], in which the inorganic nanoparticles are metal nanoparticles.

[3] The electrode material for an organic semiconductor device according to [2], in which the metal nanoparticles contain at least one kind of metal selected from the group consisting of gold, silver, copper, platinum, palladium, nickel, ruthenium, indium, rhodium, tin, and zinc.

[4] The electrode material for an organic semiconductor device according to any one of [1] to [3], in which the electron-withdrawing substituent included in the organic π-conjugated ligand is at least one substituent selected from the group consisting of a tosyl group, a mesyl group, a phenyl group, an acyl group, a halogen group, a halogenated alkyl group, a halogenated alkylthio group, a halogenated aryl group, and a halogenated arylthio group.

[5] The electrode material for an organic semiconductor device according to any one of [1] to [3], in which the electron-withdrawing substituent included in the organic π-conjugated ligand is a halogenated alkylthio group or a halogenated arylthio group.

[6] The electrode material for an organic semiconductor device according to any one of [1] to [5], in which the organic π-conjugated ligand is at least one ligand selected from the group consisting of porphyrin, phthalocyanine, naphthalocyanine and derivatives thereof.

[7] The electrode material for an organic semiconductor device according to any one of [1] to [6], which is used as an electrode material for an organic thin film transistor.

[8] The electrode material for an organic semiconductor device according to [7], which is used as an electrode material for either or both of a source electrode and a drain electrode.

According to the present invention, it is possible to provide an electrode material for an organic semiconductor device which maintains excellent conductivity and of which contact properties with an organic semiconductor becomes favorable.

DESCRIPTION OF THE PREFERRED EMBODIMENTS

Hereinafter, the present invention will be described in detail.

While the explanation of the constitutional requirements which will be described below is based on the representative embodiments of the present invention, the present invention is not limited to such embodiments.

In the present specification, the numerical range indicated by "to" is used as a meaning of including numerical values denoted before and after "to" as a lower limit value and an upper limit value.

An electrode material for an organic semiconductor device of the present invention (hereinafter, abbreviated as an "electrode material of the present invention") contains inorganic nanoparticles and an organic π-conjugated ligand.

In the electrode material of the present invention, a ligand having at least one electron-withdrawing substituent (hereinafter, also referred to as an "electron-withdrawing group") is used as an organic π-conjugated ligand.

In the electrode material of the present invention, an electrode formed using inorganic nanoparticles and an organic π-conjugated ligand which has an electron-withdrawing group maintains excellent conductivity and contact properties between the electrode and an organic semiconductor become favorable as described above.

First, in order to improve the contact properties between an organic semiconductor and an electrode, it is necessary to reduce a potential barrier by making a work function of an electrode material close to a work function of an organic semiconductor. In many cases, a work function of an organic semiconductor is generally greater than or equal to 5 eV. In general, in cases of inorganic nanoparticles (for example, metal particles of silver (4.7 eV) or copper (4.8 eV)), work functions thereof are less than or equal to 5 eV which are lower than that of an organic semiconductor, and therefore, it is necessary to increase the work functions of the inorganic nanoparticles.

In general, a work function greatly depends on the surface state of a substance. Therefore, it is effective to control polarization of the surface of a substance in order to change a work function.

For this reason, the present inventors have considered that controlling polarization of ligands formed on the surfaces of particles is effective for controlling a work function in an inorganic nanoparticle material in which an organic π-conjugated ligand is used and to which it is possible to impart conductivity without removing the ligand as in the present invention.

As a result of the study, it is possible to confirm that a work function of inorganic nanoparticles (for example, metal particles of silver or copper) is increased through polarization of the surfaces of particles formed by an electron-withdrawing group in a case where an organic π-conjugated ligand having the electron-withdrawing group is used as a ligand of an inorganic nanoparticle. Accordingly, it is possible to reduce an energy barrier of charge movement at the interface between an electrode and an organic semiconductor, to be produced, by making the work function of the inorganic nanoparticles close to the work function (approximately greater than or equal to 5 eV) of the organic semiconductor.

From results shown in Comparative Examples 1 to 3 to be described below as reverse actions, it has been found that, in a case where an organic π-conjugated ligand having an electron-donating substituent is used, a work function is decreased even though conductivity is favorable, and an energy barrier at the interface with an organic semiconductor is increased.

Next, inorganic nanoparticles and an organic π-conjugated ligand which are contained in the electrode material of the present invention, and arbitrary components will be described in detail.

[Inorganic Nanoparticles]

Inorganic nanoparticles contained in the electrode material of the present invention are not particularly limited, and it is possible to use metal nanoparticles, metal oxide particles, and the like which are well-known in the related art.

In the present invention, inorganic nanoparticles are preferably metal nanoparticles for the reason that conductivity of an electrode to be formed becomes more favorable. Specifically, the inorganic nanoparticles are more preferably metal nanoparticles containing at least one kind of metal selected from the group consisting of gold (Au), silver (Ag), copper (Cu), platinum (Pt), palladium (Pd), nickel (Ni), ruthenium (Ru), indium (In), rhodium (Rh), tin (Sn), and zinc (Zn).

Among them, metal nanoparticles containing Ag or Cu are preferable from the viewpoint of practical use and cost. In a case where metal nanoparticles contain Cu, it is preferable that the metal nanoparticles further contain metal elements (Ag, Pd, Pt, and Au) having a reduction potential higher than that of Cu from the viewpoint of oxidation resistance.

Specific examples of Ag raw materials include $Ag(NO_3)$, AgCl, $Ag(HCOO)$, $AG(CH_3COO)$, $Ag(CH_3CH_2COO)$, $Ag_2CO_3$, and $Ag_2SO_4$, these may be used singly or two or more thereof may be used in combination.

Specific examples of Cu raw materials include $Cu(NO_3)_2$, $CuCl_2$, $Cu(HCOO)_2$, $Cu(CH_3COO)_2$, $Cu(CH_3CH_2COO)_2$, $CuCO_3$, $CuSO_4$, and $C_5H_7CuO_2$, and these may be used singly or two or more thereof may be used in combination.

On the other hand, specific examples of metal oxide particles include indium tin oxide (ITO) particles, antimony tin oxide (ATO) particles, zinc oxide (ZnO which may be doped with Al) particles which may be doped with aluminum, fluorine-doped tin dioxide (F-doped $SnO_2$) particles, and niobium-doped titanium dioxide (Nb-doped $TiO_2$) particles, and these may be used singly or two or more thereof may be used in combination.

The average particle diameter of such inorganic nanoparticles is not particularly limited since it varies depending on the material constituting the particle, but is preferably 3 nm to 500 nm and more preferably 5 nm to 50 nm.

Here, the average particle diameter of inorganic nanoparticles can be obtained by measuring the particle diameters of inorganic nanoparticles in a dispersion medium using a transmission electron microscope (TEM). It is possible to calculate the average particle diameter for example, by measuring the particle diameters of 300 independent metal nanoparticles which do not overlap with each other among the particles observed in a TEM image.

In the present invention, inorganic nanoparticles are preferably dispersed in a solvent containing an amine (hereinafter, referred to as an "amine solvent") in advance before being mixed with an organic π-conjugated ligand to be described below from the viewpoints of improving dispersibility and subjecting the inorganic nanoparticles to coordination substitution (ligand substitution) with an organic π-conjugated ligand to be described below.

Specific examples of the amine solvent include alkyl amines such as nonylamine, decylamine, dodecylamine, hexadecylamine and oleylamine; and alkyl diamines such as 1,6-diaminohexane, N,N'-dimethyl-1,6-diaminohexane, 1,7-diaminoheptane, and 1,8-diaminooctane, and these may be used singly or two or more thereof may be used in combination.

It is considered that a part of amine compounds of an amine solvent are coordinated on the surfaces of inorganic nanoparticles by dispersing the inorganic nanoparticles in the amine solvent, and therefore, the dispersibility is improved.

[Organic π-conjugated Ligand]

An organic π-conjugated ligand contained in the electrode material of the present invention is not particularly limited as long as the organic π-conjugated ligand is an organic π-conjugated ligand having an electron-withdrawing group.

In the present invention, it is possible to increase a work function of the above-described inorganic nanoparticles by allowing the organic π-conjugated ligand to have an electron-withdrawing group as described above.

Specific examples of the electron-withdrawing groups include a tosyl group (—Ts), a mesyl group (—Ms), a phenyl group (—Ph), an acyl group (—Ac), a halogen group (for example, —F, —Cl, —Br, and —I), a halogenated alkyl group [—R—X (R represents an alkylene group and X represents a halogen atom)], a halogenated alkylthio group [—S—R—X (R represents an alkylene group and X represents a halogen atom)], a halogenated aryl group [—Ar—X (Ar represents an aryl group and X represents a halogen atom)], and a halogenated arylthio group [—S—Ar—X (Ar represents an aryl group and X represents a halogen atom)], and these functional groups may be provided singly, or two or more groups or two or more types thereof may be provided.

Among them, bonding between an electron-withdrawing group and an organic π-conjugated ligand is preferably performed using a sulfur atom for reasons of improving the solubility and coordinating properties to metal and a significant effect of increasing a work function. Specifically, a halogenated alkylthio group or a halogenated arylthio group is preferable.

In the present invention, the organic π-conjugated ligand is preferably at least one ligand selected from the group consisting of porphyrin, phthalocyanine, naphthalocyanine and derivatives thereof for the reason of being easily close to the above-described inorganic nanoparticles.

In the present invention, the organic π-conjugated ligand having an electron-withdrawing group is preferably a phthalocyanine compound having a halogen group and is more preferably, for example, a phthalocyanine derivative represented by the following Formula (1).

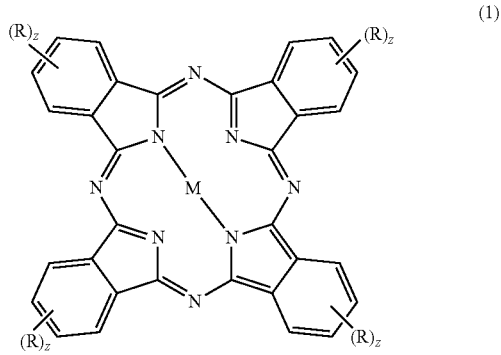

(1)

Here, in the above-described Formula (1), M represents two hydrogen atoms or metal (cation) selected from the groups 1B, 2B, 2A, or 3A of the element periodic table.

In addition, R represents a halogenated alkyl group, a halogenated alkylthio group, a halogenated aryl group, or a halogenated arylthio group. In a case where there are a plurality of R's, the plurality of R's may be the same as or different from each other.

In addition, Z represents an integer of 0 to 4 and at least one Z represents an integer of 1 to 4.

[Arbitrary Component]

The electrode material of the present invention may contain the above-described amine solvent or other organic solvents from the viewpoint of operability of coating a substrate therewith.

Examples of other organic solvents include acetone, methyl ethyl ketone, cyclohexane, cyclopentanone, ethyl acetate, ethylene dichloride, tetrahydrofuran, pentane, hexane, heptane, 2,2,2,4-trimethylpentane, octane, nonane, decane, undecane, dodecane, tridecane, tetradecane, pentadecane, toluene, xylene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 3-methoxypropanol, methoxymethoxy ethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethylformamide, dimethyl sulfoxide, γ-butyrolactone, methyl lactate, and ethyl lactate, and these may be used singly or two or more thereof may be used in combination.

The method for preparing an electrode material of the present invention is not particularly limited, and it is possible to prepare the electrode material, for example, by mixing the above-described organic π-conjugated ligand with a dispersion containing the above-described inorganic nanoparticles. However, it is preferable to prepare an electrode material by coordinating the organic π-conjugated ligand on the surfaces of the inorganic nanoparticles by subjecting the inorganic nanoparticles to ligand substitution during the mixing.

[Usage]

In the electrode material of the present invention, it is possible to form an electrode having excellent contact properties with an organic semiconductor. Therefore, the electrode material of the present invention is useful as an electrode material for printed electronics and is preferably used, for example, as an electrode material of an organic thin film transistor. Specifically, it is preferable to use the electrode material of the present invention as an electrode material for either or both of a source electrode and a drain electrode of the organic thin film transistor.

[Method for Producing Electrode]

In the electrode material of the present invention, it is possible to produce an electrode only through a wet process performed through coating, and a sintering treatment is also unnecessary after the coating since an organic π-conjugated ligand is used.

Here, the method for performing coating on a substrate (also including insulating film or an organic semiconductor layer in the case of the organic thin film transistor) is not particularly limited, and examples thereof include a printing method (for example, a gravure printing method, a screen printing method, a flexographic printing method, an inkjet printing method, and an imprinting method), a spin coating method, a slit coating method, a slit and spin coating method, a dip coating method, and a curtain coating method.

EXAMPLES

The present invention will be described in more detail based on the following Examples. The material, the usage, the proportion, treatment contents, a treatment procedure, and the like shown in Examples below can be appropriately modified without departing from the gist of the present invention. Accordingly, the scope of the present invention should not be restrictively interpreted using Examples shown below.

Example 1

<Preparation of Inorganic Nanoparticles (Ag Particles)>

90 ml of oleylamine and 1.04 g of silver nitrate ($AgNO_3$) were added to a three-neck flask. After performing vacuum deaeration, nitrogen substitution was performed.

Next, the mixture was heated to 180° C. and was reacted for 1 hour. Thereafter, the reaction solution was cooled down through air cooling to prepare a particle dispersion in which Ag particles (average particle diameter: 10.79 nm) were dispersed in oleylamine.

<Preparation of Electrode Material>

The prepared Ag particle dispersion was mixed with phthalocyanine of which M was two hydrogen atoms, R was an electron-withdrawing trifluoromethylthio group ($-SCF_3$), and Z was 2 in the above-described Formula (1), and ligand substitution was performed. Thereafter, the mixture was dispersed again in toluene to prepare an electrode material in which phthalocyanine was coordinated on the surfaces of Ag particles.

Example 2

<Preparation of Inorganic Nanoparticles (Cu Particles)>

90 ml of oleylamine and 1.55 g of copper acetylacetonate ($C_5H_7CuO_2$) were added to a three-neck flask. After performing vacuum deaeration, nitrogen substitution was performed.

Next, the mixture was heated to 240° C. and was reacted for 3 hours. Thereafter, the reaction solution was cooled down through air cooling to prepare a Cu particle dispersion in which Cu particles (average particle diameter: 17.23 nm) were dispersed in oleylamine.

<Preparation of Electrode Material>

The Prepared Cu particle dispersion was mixed with phthalocyanine of which M was two hydrogen atoms, R was an electron-withdrawing trifluoromethylthio group ($-SCF_3$), and Z was 2 in the above-described Formula (1), and ligand substitution was performed. Thereafter, the mixture was dispersed again in toluene to prepare an electrode material in which phthalocyanine was coordinated on the surfaces of Cu particles.

Comparative Example 1

An electrode material in which phthalocyanine was coordinated on the surfaces of Ag particles was prepared through the same method as that in Example 1 except that phthalocyanine of which M was two hydrogen atoms, R was an electron-donating methylthio group ($-SCH_3$), and Z was 2 in the above-described Formula (1) was used instead of phthalocyanine used in Example 1.

Comparative Example 2

An electrode material in which phthalocyanine was coordinated on the surfaces of Cu particles was prepared through the same method as that in Example 2 except that phthalocyanine of which M was two hydrogen atoms, R was an electron-donating methylthio group ($-SCH_3$), and Z was 2 in the above-described Formula (1) was used instead of phthalocyanine used in Example 2.

Comparative Example 3

An electrode material in which phthalocyanine was coordinated on the surfaces of Ag particles was prepared through the same method as that in Example 1 except that phthalocyanine (OTAP represented by the following Formula) of which M was two hydrogen atoms, R was an electron-donating dimethylaminoethanethiol group ($-SCH_2CH_2N(CH_3)_2$), and Z was 2 in the above-described Formula (1) was used instead of phthalocyanine used in Example 1. The OTAP represented by the following Formula was the organic π-conjugated ligand (organic π-bonded ligand) disclosed in WO2011/114713A and JP2014-236064A as a preferred embodiment.

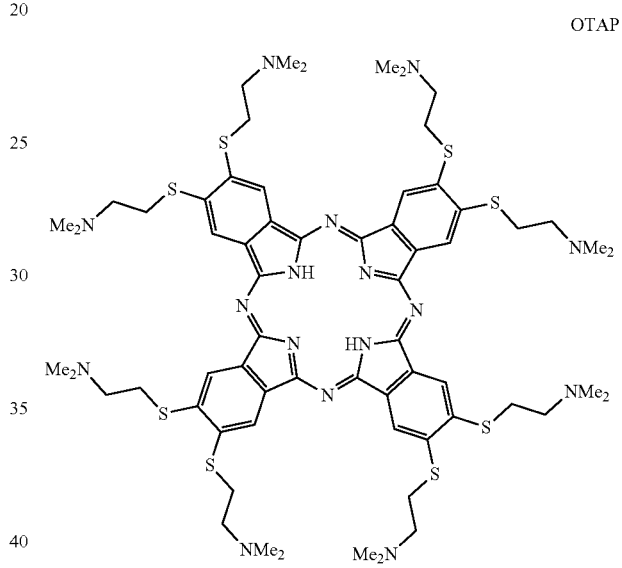

OTAP

Comparative Example 4

An electrode material in which oleylamine was coordinated on the surfaces of Ag particles was prepared through the same method as that in Example 1 except that no organic π-conjugated ligand (phthalocyanine) was used and no ligand substitution was performed during the preparation of the electrode material of Example 1.

Comparative Example 5

An electrode material in which oleylamine was coordinated on the surfaces of Cu particles was prepared through the same method as that in Example 2 except that no organic π-conjugated ligand (phthalocyanine) was used and no ligand substitution was performed during the preparation of the electrode material of Example 2.

The work function, the conductivity, and the electrode performance of each of the produced electrode materials were evaluated through the methods shown below. Results thereof are shown in the following Table 1.

<Work Function>

A glass substrate was coated with a toluene dispersion of each of the obtained electrode materials through spin coating and the coating was dried for 1 hour at 60° C. Then, a work function was measured using AC2 (manufactured by RIKEN KEIKI Co., Ltd.).

The difference between the measured work function and the work function of each inorganic nanoparticle itself in cases of using Ag (4.7 eV) and Cu (4.8 eV) are shown in the following Table 1. For example, the work function was measured as 5.4 eV in Example 1, and therefore, +0.7 eV is denoted as a difference between the measured work function and the work function (4.7 eV) of an Ag particle itself.

<Conductivity>

The conductivity of the coated film on each glass substrate used for measuring the work function was evaluated.

The evaluation was performed by regarding a case where a resistivity was less than $1 \times 10^{-2}$ Ωcm as "A" indicating excellent conductivity and regarding a case where a resistivity was greater than or equal to $1 \times 10^{-2}$ Ωcm as "B" indicating deteriorated conductivity using LORESTA manufactured by Mitsubishi Chemical Corporation.

<Electrode Performance>

A N⁺silicon substrate on which a thermal oxide film (thickness: 350 nm) was formed was coated with a toluene dispersion of each of the obtained electrode materials using an inkjet apparatus (manufactured by DIMATIX) to form a source electrode and a drain electrode which have a thickness of 100 nm. Thereafter, an organic semiconductor (C8-BTBT manufactured by Sigma-Aldrich Co., LLC) having a thickness of 50 nm was formed and a bottom gate/bottom contact type organic thin film transistor was produced.

TFT characteristics were measured using a semiconductor parameter analyzer (Agilent 4155 manufactured by Agilent). A case of an on-off ratio greater than or equal to 4 digits was evaluated as "A" and a case of an on-off ratio less than 4 digits was evaluated as "B".

tron-withdrawing substituent was used, the work function was increased while maintaining excellent conductivity and the electrode performance was also favorable, and therefore, the contact properties with an organic semiconductor was favorable (Examples 1 and 2).

What is claimed is:

1. An electrode material for an organic semiconductor device, comprising:
    inorganic nanoparticles and an organic π-conjugated ligand,
    wherein the organic π-conjugated ligand is a phthalocyanine derivative represented by Formula (1) below and has at least one electron-withdrawing substituent R,

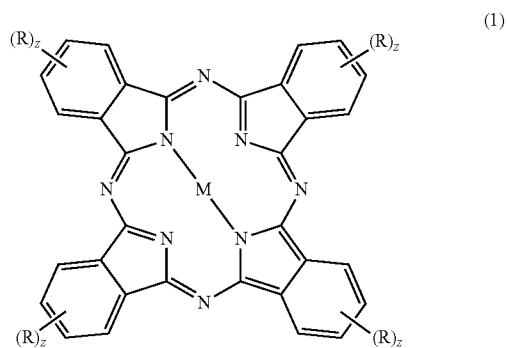

wherein in Formula (1), M represents two hydrogen atoms or metal (cation) selected from the groups 1B, 2B, 2A, or 3A of the element periodic table; R represents a halogenated alkyl group, a halogenated alkyl-

TABLE 1

|  | Inorganic nanoparticle | Organic π-conjugated ligand | | Work function | Conductivity | Electrode performance |
| --- | --- | --- | --- | --- | --- | --- |
|  |  | Ligand | Substituent |  |  |  |
| Example 1 | Ag | Phthalocyanine | Trifluoromethylthio group | +0.7 eV | A | A |
| Example 2 | Cu | Phthalocyanine | Trifluoromethylthio group | +0.5 eV | A | A |
| Comparative Example 1 | Ag | Phthalocyanine | Methylthio group | −0.2 eV | A | B |
| Comparative Example 2 | Cu | Phthalocyanine | Methylthio group | −0.5 eV | A | B |
| Comparative Example 3 | Ag | Phthalocyanine (OTAP) | Dimethylaminoethanethiol group | −0.2 eV | A | B |
| Comparative Example 4 | Ag | (Oleylamine) |  | −0.3 eV | B | B |
| Comparative Example 5 | Cu | (Oleylamine) |  | −0.3 eV | B | B |

It was found that, when an electrode material containing phthalocyanine having an electron-donating substituent was used, even though the conductivity was favorable, the work function and the electrode performance were deteriorated as shown in Table 1, and therefore, contact properties with an organic semiconductor was inferior (Comparative Examples 1 to 3).

In addition, it was found that, when an electrode material in which no organic π-conjugated ligand was used, was used, the conductivity and the work function were deteriorated, and the electrode performance was also deteriorated (Comparative Examples 4 and 5).

In contrast, it was found that, when an electrode material containing an organic π-conjugated ligand having an electhio group, a halogenated aryl group, or a halogenated arylthio group and in a case where there are a plurality of R's, the plurality of R's may be the same as or different from each other; and z represents an integer of 0 to 4 and at least one z represents an integer of 1 to 4.

2. The electrode material for an organic semiconductor device according to claim 1,
    wherein the inorganic nanoparticles are metal nanoparticles.

3. The electrode material for an organic semiconductor device according to claim 2,
    wherein the metal nanoparticles contain at least one kind of metal selected from the group consisting of gold, silver, copper, platinum, palladium, nickel, ruthenium, indium, rhodium, tin, and zinc.

4. The electrode material for an organic semiconductor device according to claim 1, which is used as an electrode material for an organic thin film transistor.

5. The electrode material for an organic semiconductor device according to claim 2, which is used as an electrode material for an organic thin film transistor.

6. The electrode material for an organic semiconductor device according to claim 3, which is used as an electrode material for an organic thin film transistor.

7. The electrode material for an organic semiconductor device according to claim 4, which is used as an electrode material for either or both of a source electrode and a drain electrode.

8. The electrode material for an organic semiconductor device according to claim 5, which is used as an electrode material for either or both of a source electrode and a drain electrode.

9. The electrode material for an organic semiconductor device according to claim 6, which is used as an electrode material for either or both of a source electrode and a drain electrode.

\* \* \* \* \*